(12) United States Patent
Falahee

(10) Patent No.: US 8,088,148 B2
(45) Date of Patent: Jan. 3, 2012

(54) DYNAMIC/STATIC FACET FIXATION DEVICE AND METHOD

(75) Inventor: Mark H. Falahee, Ann Arbor, MI (US)

(73) Assignee: Medical Design, LLC, Ann Arbor, MI (US)

( * ) Notice: Subject to any disclaimer, the term of this patent is extended or adjusted under 35 U.S.C. 154(b) by 827 days.

(21) Appl. No.: 11/678,713

(22) Filed: Feb. 26, 2007

(65) Prior Publication Data

US 2007/0233092 A1 Oct. 4, 2007

Related U.S. Application Data

(60) Provisional application No. 60/776,451, filed on Feb. 24, 2006.

(51) Int. Cl.
*A61B 17/70* (2006.01)
(52) U.S. Cl. ........................... 606/247; 606/246
(58) Field of Classification Search ............ 606/30–321; 623/17.11, 17.16
See application file for complete search history.

(56) References Cited

U.S. PATENT DOCUMENTS

| | | | | |
|---|---|---|---|---|
| 5,702,397 A * | 12/1997 | Goble et al. | ................ | 606/232 |
| 6,986,771 B2 * | 1/2006 | Paul et al. | ................ | 606/254 |
| 7,846,183 B2 * | 12/2010 | Blain | ................ | 606/247 |
| 2002/0040222 A1 * | 4/2002 | Hashimoto et al. | ................ | 606/61 |
| 2005/0049705 A1 * | 3/2005 | Hale et al. | ................ | 623/17.11 |
| 2005/0203522 A1 * | 9/2005 | Vaughan | ................ | 606/73 |

* cited by examiner

*Primary Examiner* — Eduardo C Robert
*Assistant Examiner* — Christina Negrelli
(74) *Attorney, Agent, or Firm* — Gifford, Krass, Sprinkle, Anderson & Citkowski, P.C.

(57) ABSTRACT

A facet fixation system facilitates dynamic or static stabilization with few exposed components. A first anchor component is adapted for implantation through a facet joint and into intra-pedicle bone, and a second anchor component is adapted for fixation to the outer surface of the facet joint. A connector component connects the first and second anchor components. The connector component may be at least partially elastic, facilitating a dynamic stabilization of a facet joint, or rigid, facilitating a static stabilization of a facet joint.

5 Claims, 4 Drawing Sheets

DYNAMIC/STATIC FACET FIXATION DEVICE AND METHOD

REFERENCE TO RELATED APPLICATION

This application claims priority from U.S. Provisional Patent Application Ser. No. 60/776,451, filed on Feb. 24, 2006, the entire content of which is incorporated herein by reference.

FIELD OF THE INVENTION

This invention relates generally to spinal stabilization and, in particular, to a spinal implant placed across a facet joint via opener microsurgical techniques that allows for either dynamic (motion preserving) or static (no motion) stabilization.

BACKGROUND OF THE INVENTION

Various facet fixation techniques are known to those of skill in the art. The universal cannulated screw system of Medtronics includes a translaminar cannulated screw that is placed by guide wire across the facet joint from an entry point at the spinous process/laminate junction. This is opposite the actual facet joint, closing through the lamina and facet joint proper. The system provides only for static stabilization using a translaminar, open approach, with significant dissection. The fixation is non-locking.

The Nuvasive facet fixation system is a non-translaminar approach utilizing a single screw through the facet joint and trajectory down into the pedicle. The screw pathway is oblique to the joint surface. Although open or micro techniques may be used, the system is non-locking and limited to static fixation.

The Dynasys system from Zimmer, which is a dynamic pedicle fixation device, utilizes pedicle screws attached to an elastic-type "rod" covered in a silicone spacer. The system is dynamic only and must use an open technique. The facet joint is not involved.

SUMMARY OF THE INVENTION

This invention resides in a facet fixation system that facilitates dynamic or static stabilization with few exposed components. A first anchor component is adapted for implantation through a facet joint and into intra-pedicle bone, and a second anchor component is adapted for fixation to the outer surface of the facet joint. A connector component connects the first and second anchor components. The connector component may be at least partially elastic, facilitating a dynamic stabilization of a facet joint, or rigid, facilitating a static stabilization of a facet joint.

DETAILED DESCRIPTION OF THE INVENTION

Figure 1:
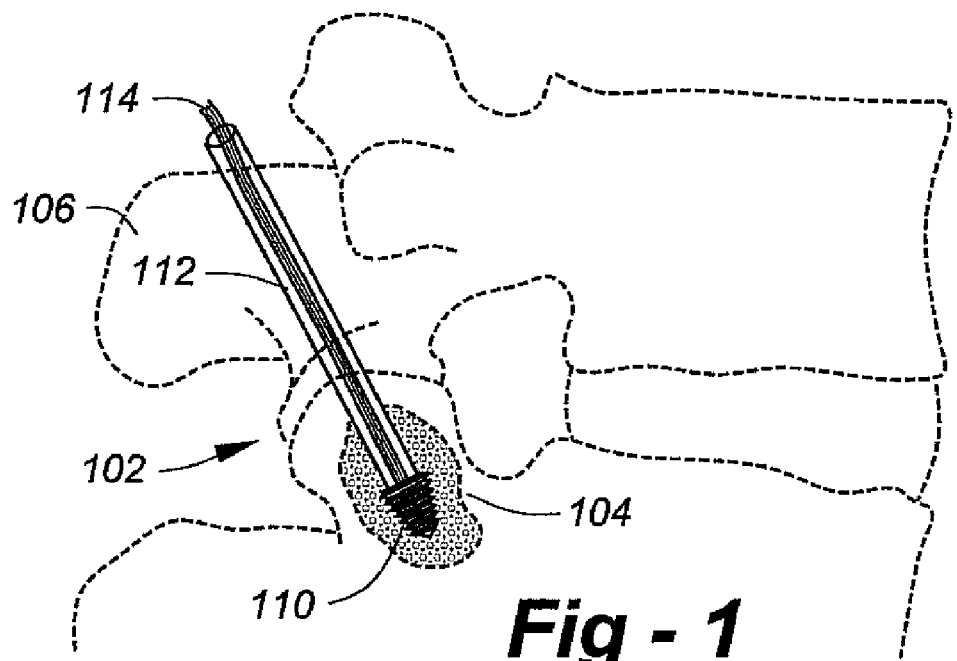
FIG. 1 is a side-view drawing showing the facet joint in the first stage of a procedure utilizing the instant invention.
Figure 2:
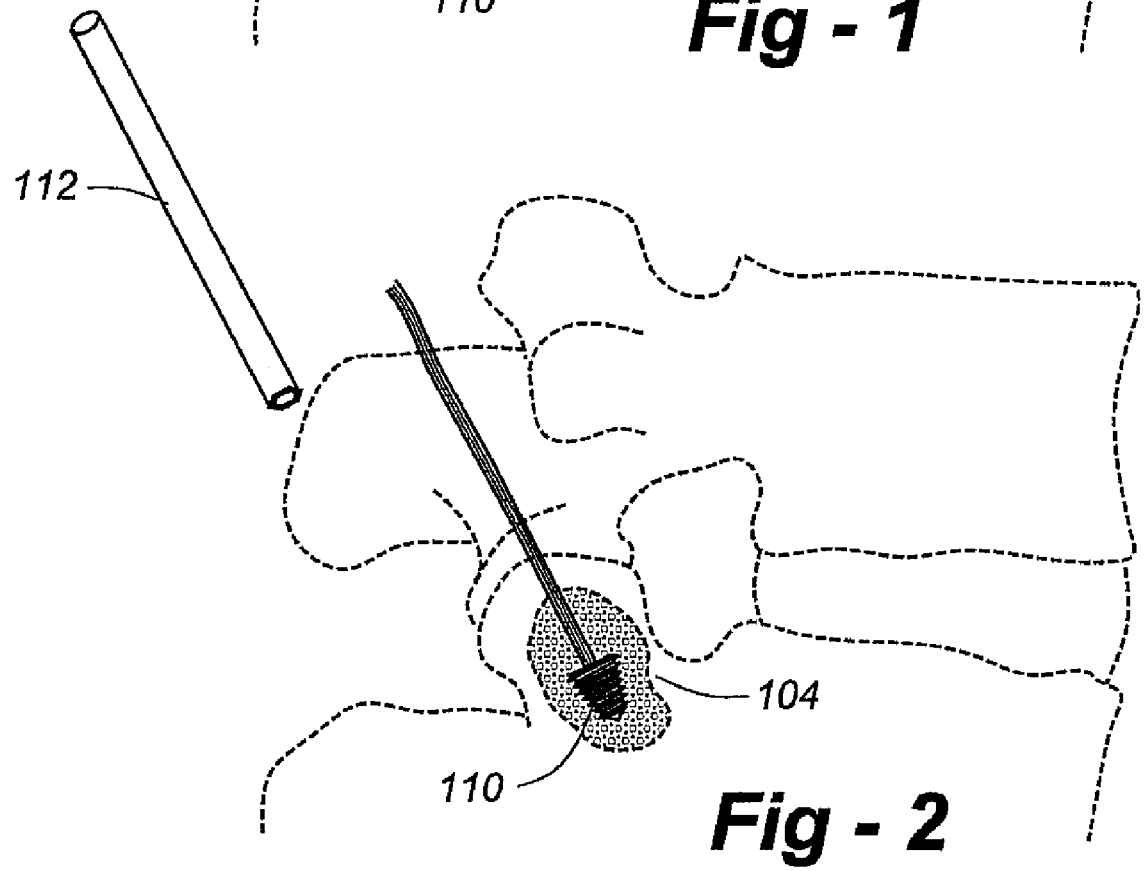
FIG. 2 shows the initial introducer removed, leaving elastic cord connected to an implanted anchor.

FIG. 1 is a drawing which shows an initial procedure according to the invention for the introduction of a dynamic facet stabilization system. Using a non-translaminar approach, a screw 110, preferably conical in shape, is placed perpendicular to the facet joint surface and advanced into intra-pedicle bone 104. An elastic cord (i.e., surgi-cord, "bungee" cord) 114 is attached to the screw 110. The facet joint is indicated generally at 102. Item 106 is the spinous process for the upper vertebral body. Item 112 is an introduction tool that is removed after placement of the anchor screw, as shown in FIG. 2.

Figure 3:
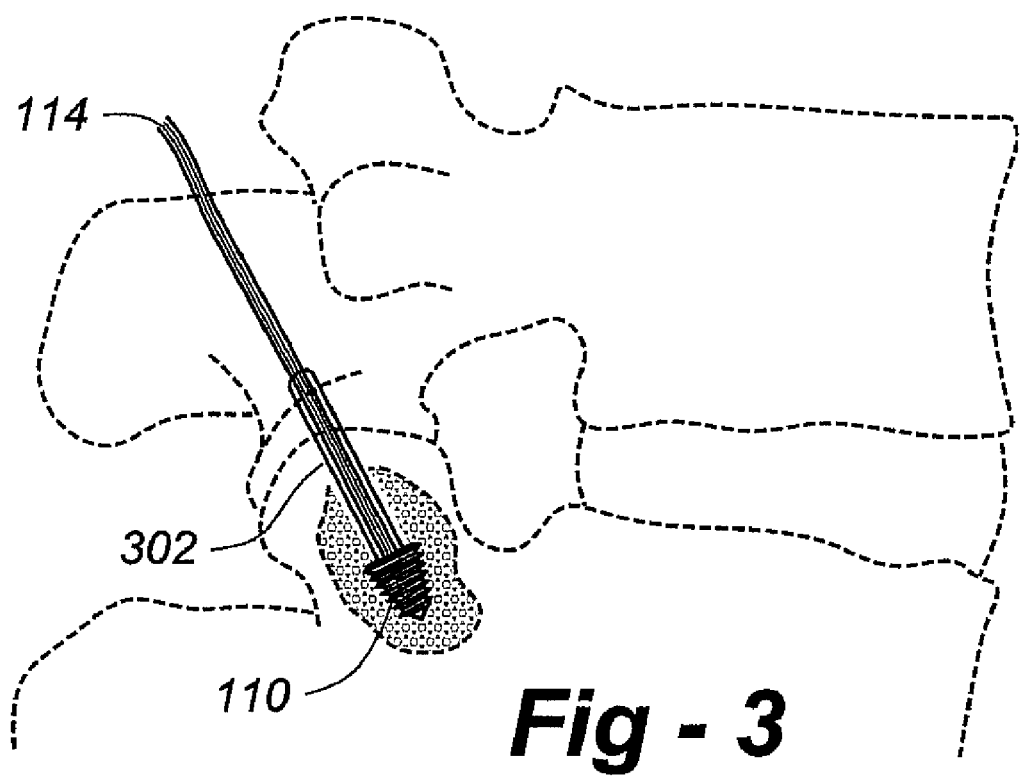
FIG. 3 illustrates the introduction of a silicone or gliding material sleeve placed over the elastic cord.
Figure 4:
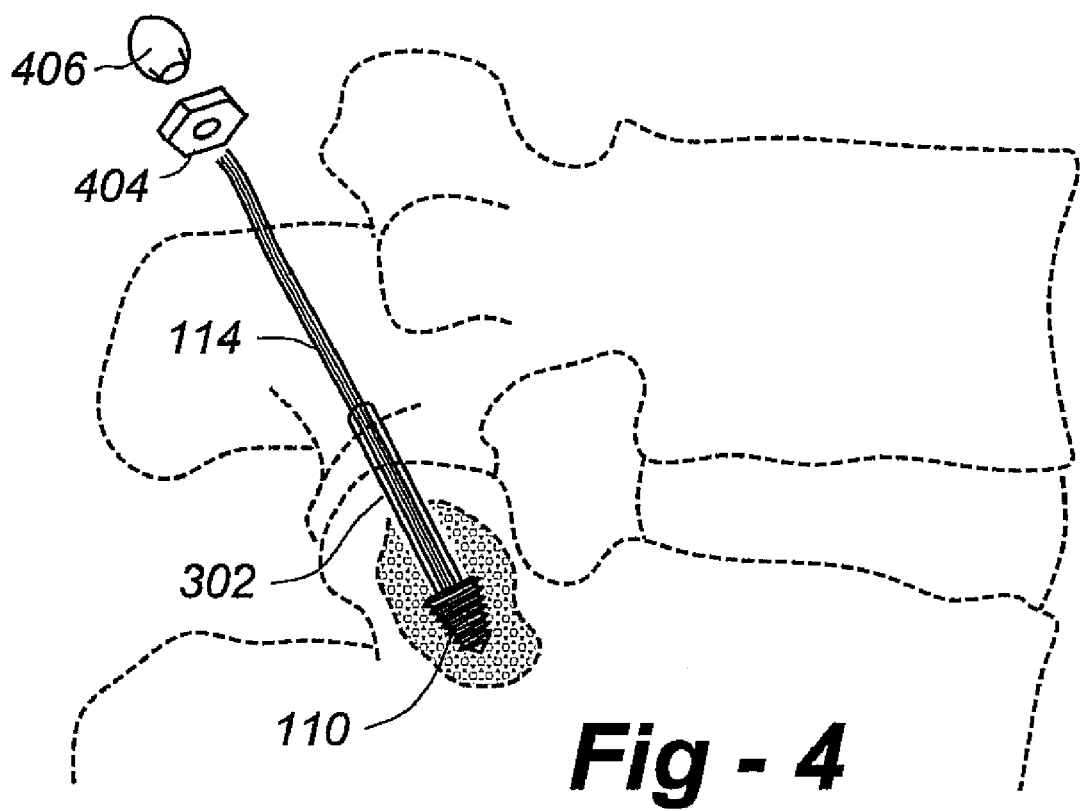
FIG. 4 shows a bottom anchor nut and fenestrated grommet being placed over the elastic cord.
Figure 5:
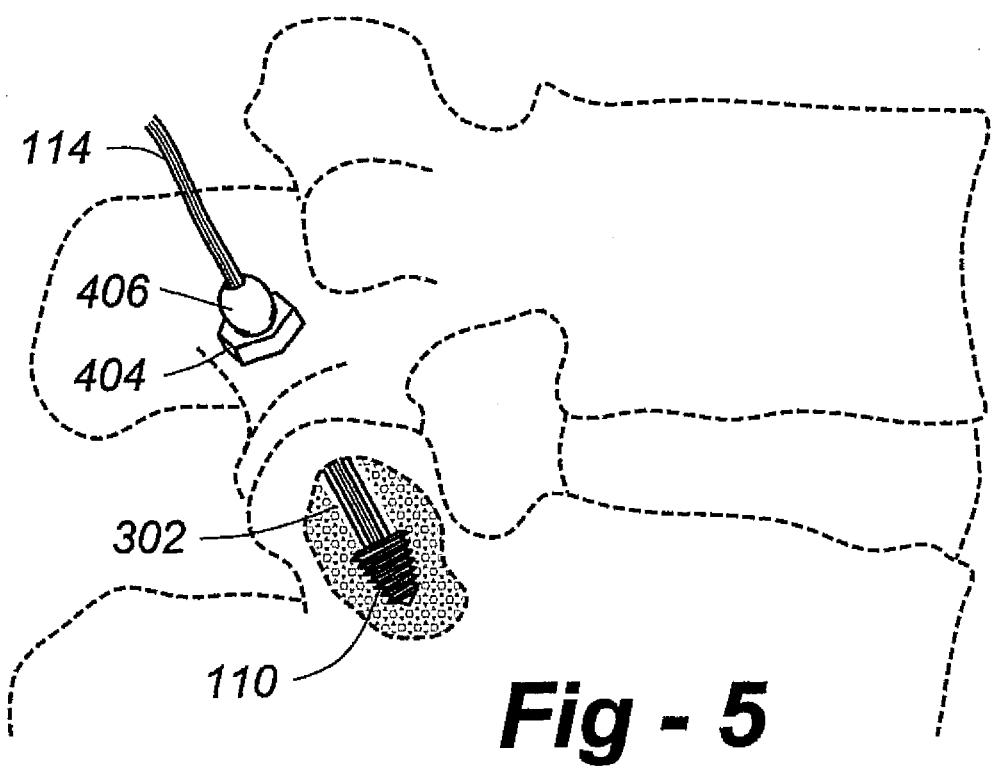
FIG. 5 shows the elastic cord in tension, with the nut assembly tightened and crimped.
Figure 6:
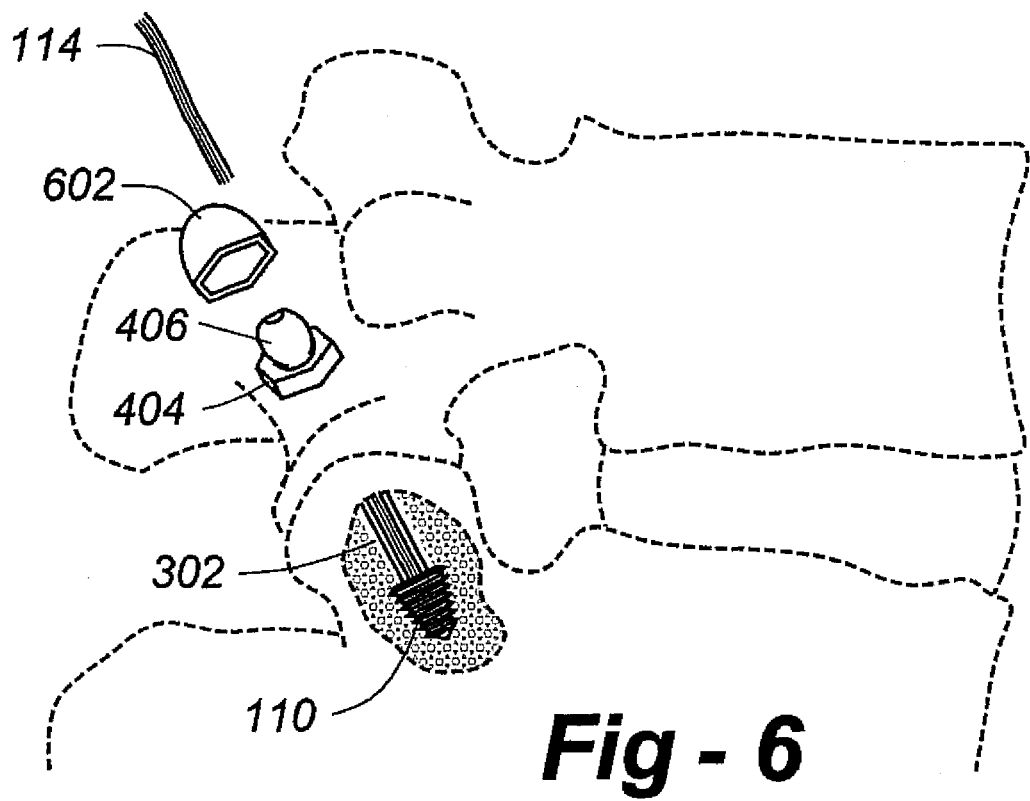
FIG. 6 shows the removal excess elastic cord, and the placement of a top cover.

Turning now to FIG. 3, to limit extension, an optional gliding sleeve 302 made of silicone or other material is placed over the cord 114 and advanced across the facet joint to the anchor screw. Following this procedure, a bottom anchor nut 404 and fenestrated grommet 406 are dressed over the cord 114. The placement is shown in FIG. 5, at which time the cord 114 is tensioned as appropriate, the grommet 406 is crimped, and excess cord material is removed as shown in FIG. 6. Also shown in FIG. 6 is the application of a top anchor nut or cap 602.

Figure 7:
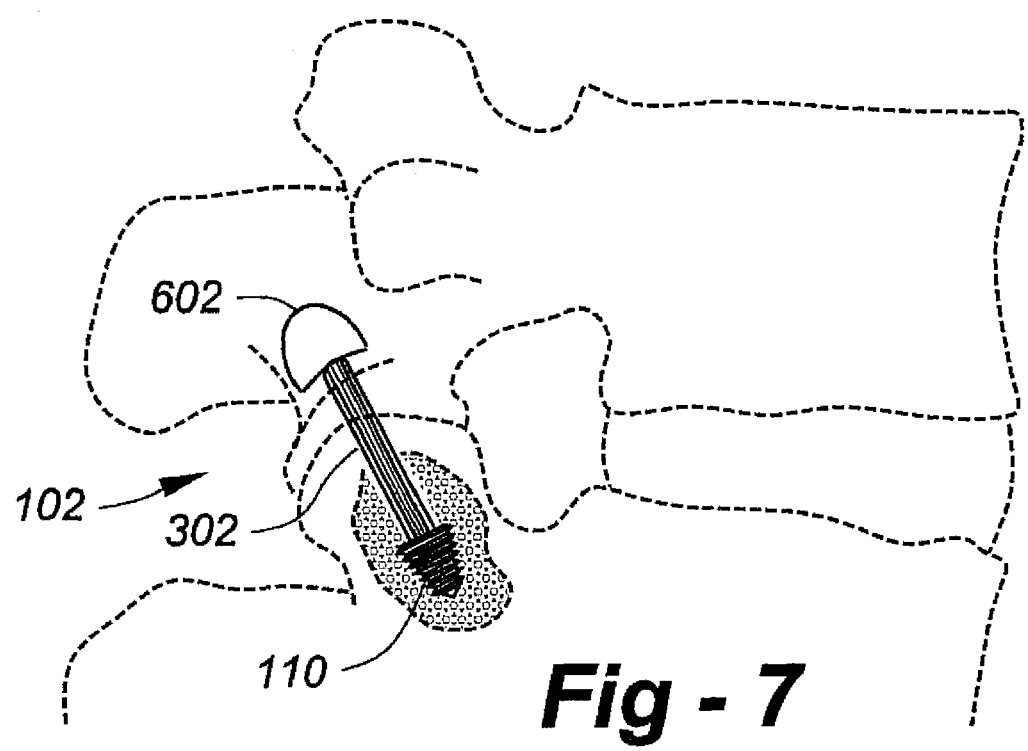
FIG. 7 shows a facet joint in neutral position, with the gliding sleeve limiting excessive extension.
Figure 8:
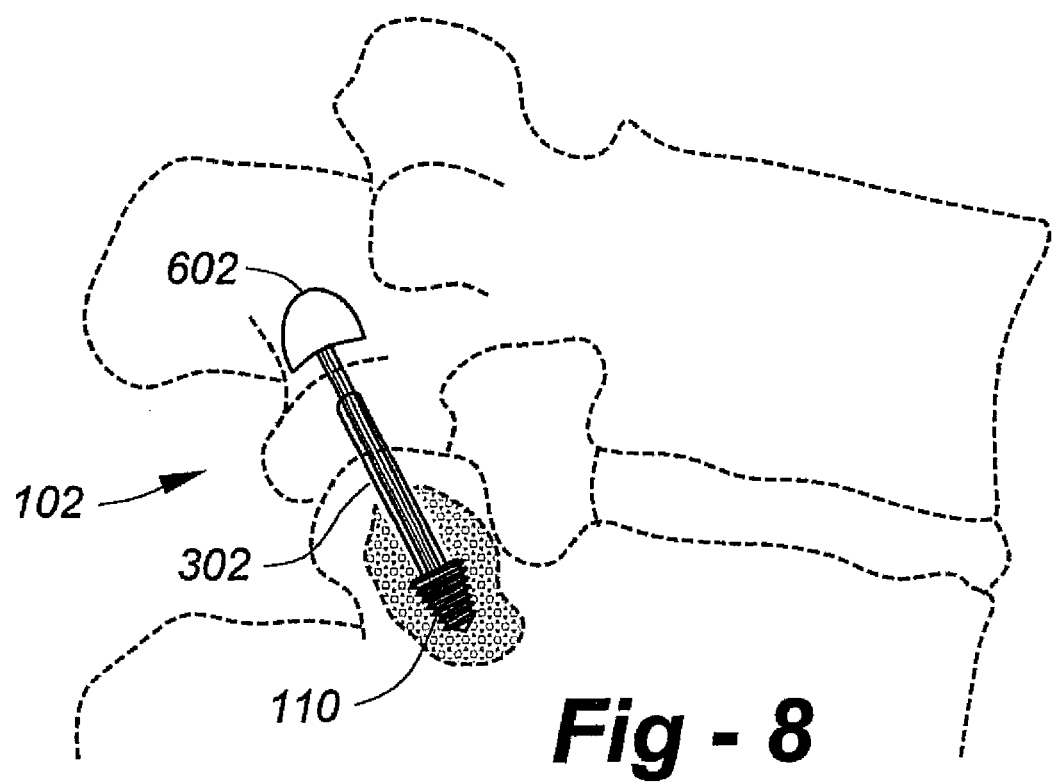
FIG. 8 shows how the elastic cord is stretched during flexion, while limiting excessive motion.

FIG. 7 shows the completed assembly in a neutral position, with the optional gliding sleeve 302 preventing excessive extension across the facet joint 102. With flexion, the elastic cord is able to extend beyond the length of the sleeve 302, but excessive flexion is limited by the tension of the cord.

Although the system just described is dynamic in nature, a static system may be created by substituting the anchor 110 and elastic cord with a fixed, solid shaft and distal anchor. A separate, low-profile top tightening nut attaches to the outer threads of the thick shaft, causing static compression across the facet joint. Indeed, according to the invention, a dynamic system may be revised to become static, if necessary.

I claim:

1. A facet fixation system, comprising:
   a first anchor component adapted for implantation through a facet joint and into intra-pedicle bone, the first anchor component including a distal screw and a cord extending proximally from the distal screw and out through the outer surface of the facet joint;
   a second anchor component adapted for fixation to the cord such that the second anchor component is disposed against the outer surface of the facet joint; and
   further including a gliding sleeve around the cord between the first and second anchor components, thereby preventing excessive extension across the facet joint.

2. A facet fixation system, comprising:
   a first anchor component adapted for implantation through a facet joint and into intra-pedicle bone, the first anchor component including a distal screw and a cord extending proximally from the distal screw and out through the outer surface of the facet joint;
   a second anchor component adapted for fixation to the cord such that the second anchor component is disposed against the outer surface of the facet joint; and
   wherein the second anchor component is fixed to the cord through a crimpable connector.

3. A facet fixation system, comprising:
- a first anchor component adapted for implantation through a facet joint and into intra-pedicle bone, the first anchor component including a distal screw and a cord extending proximally from the distal screw and out through the outer surface of the facet joint;
- a second anchor component adapted for fixation to the cord such that the second anchor component is disposed against the outer surface of the facet joint; and
- wherein the second anchor component includes an anchor nut and a fenestrated grommet that is fixed to the cord through crimping.

4. A method of stabilizing a facet joint, comprising the steps of:
- providing the facet fixation system of claim 1;
- placing the screw through a facet joint and into intra-pedicle bone such that the cord extends outwardly from the outer surface of the facet joint;
- fastening the second anchor component to the cord such that the second anchor component is disposed against the outer surface of the facet joint; and
- wherein the step of fastening the second anchor component to the cord includes placing the second anchor component over the cord and crimping the second anchor component to the cord.

5. A method of stabilizing a facet joint, comprising the steps of:
- providing the facet fixation system of claim 1;
- placing the screw through a facet joint and into intra-pedicle bone such that the cord extends outwardly from the outer surface of the facet joint;
- fastening the second anchor component to the cord such that the second anchor component is disposed against the outer surface of the facet joint; and
- including the step of placing a gliding sleeve over the cord prior to the application of the second anchor component.

* * * * *